United States Patent
Basset et al.

(10) Patent No.: US 6,727,397 B2
(45) Date of Patent: Apr. 27, 2004

(54) PROCESS FOR MANUFACTURING ALKANES WITH METHANE

(75) Inventors: Jean-Marie Basset, Caluire (FR); Christophe Coperet, Lyons (FR); Laurent Lefort, Lyons (FR); Barry Martin Maunders, Woking (GB); Olivier Maury, Rennes (FR); Guillaume Saggio, Lyons (FR); Jean Thivolle-Cazat, Fontaine/Saone (FR)

(73) Assignee: BP Chemicals Limited, London (GB)

( * ) Notice: Subject to any disclaimer, the term of this patent is extended or adjusted under 35 U.S.C. 154(b) by 113 days.

(21) Appl. No.: 10/040,495

(22) Filed: Jan. 9, 2002

(65) Prior Publication Data

US 2003/0045765 A1 Mar. 6, 2003

Related U.S. Application Data

(63) Continuation of application No. PCT/GB00/02580, filed on Jul. 5, 2000.

(30) Foreign Application Priority Data

Jul. 9, 1999 (FR) ............................................. 99 09125

(51) Int. Cl.⁷ ................................................. C07C 6/08
(52) U.S. Cl. ....................................................... 585/708
(58) Field of Search .................................. 585/208, 708

(56) References Cited

FOREIGN PATENT DOCUMENTS

| | | |
|---|---|---|
| GB | 604410 | 1/1946 |
| WO | WO 98/02244 | 1/1998 |

*Primary Examiner*—Thuan D. Dang
(74) *Attorney, Agent, or Firm*—Finnegan, Henderson, Farabow, Garrett and Dunner, L.L.P.

(57) ABSTRACT

The present invention relates to a process for manufacturing alkanes, comprising, as main stage, a reaction resulting from bringing methane into contact with at least one other starting alkane (A) in the presence of a catalyst based on a metal M capable of catalyzing a metathesis of alkanes. The reaction results in the formation of at least one or two final alkanes (B) having a number of carbon atoms less than or equal to that of the starting alkane (A) and at least equal to 2. Preferably the catalyst comprises a hydride of a metal M grafted to and dispersed over a solid support. The metal M may be chosen from transition metals, lanthanides and actinides. The present invention also relates to the use of a catalyst capable of catalyzing a metathesis of alkanes in 3 reaction resulting from bringing methane into contact with at least one other starting alkane (A).

20 Claims, No Drawings

PROCESS FOR MANUFACTURING ALKANES WITH METHANE

This is a continuation of PCT/6800/02580, filed on Jul. 5, 2000.

BACKGROUND OF THE INVENTION

The present invention relates to a process for the manufacture of alkanes by a catalytic reaction employing methane with at least one other alkane.

Alkanes, such as methane, are generally products which are difficult to employ because of their chemical inertia. Nevertheless, the conversion of alkanes into other alkanes is known. Hydrogenolysis reactions, which consist of cleavage or opening reactions of a carbon-carbon bond by hydrogen, are known, for example. Isomerization reactions, which convert an alkane into one of its isomers, for example n-butane into isobutane, are also known. All these reactions are generally carried out at relatively high temperatures and in the presence of catalysts based on metals, in particular on transition metals, in the bulk form or in the form of films or alternatively in the form of metal particles deposited on inorganic supports essentially based on metal oxide or refractory oxide. Thus, for example, the catalyst can be of the following types: nickel black, $Ni/SiO_2$, platinum black $Pt/SiO_2$, $Pd/Al_2O_3$, or tungsten or rhodium film, optionally mixed with copper, tin or silver. With some metal catalysts, it was possible simultaneously to observe alkane homologation reactions, which consist of reactions which convert alkanes into higher homologous alkanes. However, alkane homologation reactions are generally very minor reactions in comparison with the hydrogenolysis or isomerization reactions and their results are very poor.

Nevertheless, it remains the case that a process for the conversion of an alkane into one of its homologues would constitute a means for enhancing these alkanes in value, in particular methane. It is known that, as a general rule, alkanes of low molecular weight cannot be exploited to any great extent in chemistry or petrochemistry, other than as fuels, whereas heavier alkanes are often of greater commercial interest, such as, for example, to increase the octane number of engine fuels or alternatively to involve these heavier alkanes in thermal or thermal catalytic cracking or steam cracking reactions in order to manufacture, for example, olefins or dienes.

In this sense, Patent Application PCT/FR 97/01266 discloses a process for the metathesis of alkanes. A metathesis is a double decomposition reaction of two identical or different compounds which forms two new compounds by a double recombination. In this case, at least one alkane is reacted with itself or several alkanes with one another in the presence of a solid catalyst comprising a metal hydride grafted to and dispersed over a solid oxide. Thus, the metathesis reaction is carried out in the presence of this metal hydride by cleavage and recombination of the carbon-carbon bonds, converting an alkane simultaneously into its higher and lower homologues. The reaction can be written according to the following equation (1):

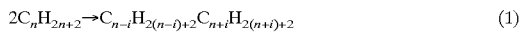

(1)

where i=1, 2, 3, . . . n−1 and n can range from 2 to 30 and even beyond.

The catalyst used is a catalyst based on metal hydride and comprises a transition metal chosen in particular from those from groups 5 and 6 of the Table of the Periodic Classification of the Elements (as defined by IUPAC in 1991 and illustrated in "Hawley's Condensed Chemical Dictionary", 12$^{th}$ edition, by Richard J. Lewis, Sr., published by Van Nostrand Reinhold Company, New York, 1993), such as, in particular, tantalum, chromium or tungsten. The preparation of the catalyst comprises a stage of hydrogenation of an organometallic precursor comprising a transition metal dispersed over and grafted to a solid oxide beforehand, so that the transition metal is reduced to an oxidation state lower than its maximum value, thus resulting in the metal hydride. However, as in any metathesis of alkanes, in particular carried out in the presence of this metal hydride, higher and lower homologous alkanes are simultaneously manufactured, by cleavage and recombination reactions of carbon-carbon bonds, employing at least $C_2$ alkanes (ethane).

SUMMARY OF THE INVENTION

A novel process for the manufacture of alkanes has now been found which makes use of a reaction resulting from bringing methane into contact with at least one other starting alkane in the presence of a catalyst capable of catalysing a metathesis of alkanes. The process has the advantage of enhancing the value of methane, which is available in large amounts on the market and is known for being used essentially as a fuel. Finally, the process makes possible the direct manufacture of the desired product without forming a large number of by-products and thus makes it possible to avoid or to cut back on lengthy and expensive operations for the separation and isolation of the desired product.

A subject-matter of the invention is therefore a process for the manufacture of alkanes, characterized in that it comprises, as main stage, a reaction resulting from bringing methane into contact with at least one other starting alkane (A) in the presence of a catalyst based on a metal M capable of catalysing a metathesis of alkanes, which reaction results in the formation of at least one or two final alkanes (B) having a number of carbon atoms less than or equal to that of the starting alkane (A) and at least equal to 2.

DETAILED DESCRIPTION OF THE INVENTION

More particularly, a catalytic reaction is carried out which results from bringing methane into contact with at least one other starting $C_n$ alkane (A) (that is to say, comprising n carbon atoms), with n being equal to at least 2, preferably to at least 3, so that the reaction results in the formation of at least one or two final $C_2$ to $C_n$ alkanes (B) (that is to say, having a number of carbon atoms ranging from 2 to n).

The reaction can be written according to one or more of the following equations (2):

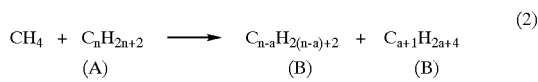

(2)

in which equation (2) n is an integer at least equal to 2, preferably at least equal to 3, and a is an integer ranging from 1 to n−1.

Thus, the process of the invention comprises, as main stage, one or more reactions resulting from bringing methane into contact with at least one other starting alkane (A), the mechanisms of which reactions have not yet been clearly determined. This is because it is particularly surprising to find that methane, which does not comprise a carbon-carbon bond, can react directly or indirectly with another starting alkane (A) in the presence of a catalyst capable of catalysing a reaction for the metathesis of alkanes by cleavage and recombination of the carbon-carbon bonds. The reaction employed in the process of the present invention is carried out by simply bringing methane into contact with at least one other starting alkane (A) in the presence of a catalyst for the metathesis of alkanes and under relatively mild conditions, as described a little later.

The starting alkane (A) can be a substituted or unsubstituted acyclic alkane, that is to say composed of a linear or branched but unclosed carbon-comprising chain. It can correspond to the general formula:

$$C_nH_{2n+2} \tag{3}$$

in which n is an integer ranging from 2 to 60 or from 3 to 60, preferably from 3 to 50, in particular from 3 to 20.

The starting alkane (A) can also be a cyclic alkane or cycloalkane substituted in particular by a linear or branched carbon-comprising chain, for example by an alkyl radical. It can correspond to the general formula:

$$C_nH_{2n} \tag{4}$$

in which n is an integer ranging from 5 to 60, preferably from 5 to 20, in particular from 5 to 10.

Use may be made of one or more starting alkanes (A) such as those described above.

More particularly, the starting alkane (A) can be chosen from $C_3$ to $C_{10}$ or $C_3$ to $C_{17}$ alkanes, for example propane, n-butane, isobutane, n-pentane, isopentane, n-hexane, n-heptane, n-octane, n-nonane and n-decane.

Thus, for example, in the process of the present invention, methane can be brought into contact with propane to form ethane or alternatively methane can be brought into contact with n-butane ethane and propane.

The staring alkane (A) can also be chosen from paraffins, such as n-paraffins, isoparaffins and cycloparaffins, for example $C_{18}$ to $C_{60}$ or $C_{22}$ to $C_{60}$ or alternatively $C_{22}$ to $C_{45}$ n-paraffins, isoparaffins and cycloparaffins.

Methane is brought into contact with at least one other starting alkane (A) in the presence of a catalyst based on a metal M capable of or known for catalysing a metathesis of alkanes. It is in particular a catalyst which, if it were brought into contact with at least one alkane, for example a $C_2$ to $C_{30}$ alkane, would result in a metathesis of the alkane as represented by the equation (1). It can in particular be a catalyst comprising a hydride of a metal M grafted to and dispersed over a solid support, such as a metal oxide or sulphide or refractory oxide or sulphide Without it being possible to explain in detail the catalytic mechanism of the main reaction of the process of the present invention, it is likely to imagine the catalyst as acting as a catalytic intermediate When it is brought into contact with methane, the catalyst can probably form a methyl-metal M complex, which might be the catalytically active species with regard to the starting alkane (A).

The catalyst comprises, for example, a solid support to which are grafted and over which are dispersed metal atoms of the metal M which are found in the hydride form. Thus, the catalyst preferably comprises a metal M bonded to at least one hydrogen atom.

The metal M can be chosen from transition metals, in particular the metals from columns 3, 4, 5 and 6 of the Table of the Periodic Classification of the Elements mentioned above, and from lanthanides and actinides. The metal can, for example, be chosen from scandium, yttrium, lanthanum, titanium, zirconium, hafnium, vanadium, niobium, tantalum, chromium, molybdenum, tungsten, cerium and neodymium.

Preference is given to a metal chosen from the transition metals of the abovementioned columns 4, 5 and 6 and in particular from titanium, zirconium, hafnium, vanadium, niobium tantalum, chromium, molybdenum and tungsten. More particularly, preference is given to tantalum, chromium, vanadium, niobium, molybdenum or tungsten.

The metal M present in the catalyst in the hydride form and attached to the solid support is generally at an oxidation state lower than its maximum value. It can, for example, be at an oxidation state lower by 1 or 2 points than its maximum value. In particular, the metal can be in a state of advanced electronic unsaturation: its valence layer can be highly deficient in electrons (less than 16 electrons); in the cases observed, there are approximately 10 electrons.

The metal hydride is attached to a solid support which can be chosen from oxides or sulphides. Preference is given to a solid support, such as a metal oxide or refractory oxide or a mixture of oxides, for example silica, alumina, a mixture of silica and alumina, zeolites, natural clays, aluminium silicates, titanium oxide, magnesium oxide, niobium oxide or zirconium oxide. The solid support can be a metal oxide or refractory oxide modified by an acid, such as a sulphated zirconia or a sulphated alumina. The solid support can also be a metal sulphide, such as a molybdenum or tungsten sulphide, a sulphurized alumina or a sulphurized metal oxide. It is preferable to use a solid support chosen from silicas and aluminas, in particular porous or non-porous silicas and aluminas, for example mesoporous silicas and aluminas having pores of 20 to 200 Å.

The solid support based on metal oxide or refractory oxide has the advantage of exhibiting, at its surface, oxygen atoms which can form part of the coordination shell of the metal M. Thus, the metal M can advantageously be bonded to one or, preferably, to at least two functional groups of the solid support. In this case, if the solid support is a metal oxide or a refractory oxide, the metal can be bonded to one or, preferably, to at least two oxygen atoms of the solid support. The presence of one or, preferably, of at least two oxygen-metal bonds confers greater stability on the metal hydride while providing a strong support-metal bond.

The catalyst described above can be prepared in various ways. One of the preparation processes can comprise the following two stages:

(a) the dispersion over and the grafting to the solid support of an organometallic precursor (P) comprising the metal M bonded to at least one hydrocarbon-comprising ligand, then (b) the treatment of the product resulting from the preceding stage with hydrogen or a reducing agent capable of forming a metal M-hydrogen bond, in particular by hydrogenolysis of the hydrocarbon-comprising ligands.

The organometallic precursor (P) comprises the metal M described above bonded to at least one hydrocarbon-comprising ligand. It can correspond to the general formula $$MR \tag{5}$$

in which M represents the metal of the catalyst as described above, R represents one or more identical or different, saturated or unsaturated, hydrocarbon-comprising ligands, in particular aliphatic or alicyclic hydrocarbon-comprising ligands, preferably from $C_1$ to $C_{20}$, especially from $C_1$ to $C_{10}$, and a is an integer equal to the oxidation state of the metal M.

The metal M in the organometallic precursor (A) can be at an oxidation state lower than or, preferably, equal to its maximum value.

The metal M can be bonded to one or more carbons of the hydrocarbon-comprising ligands R via one or more carbon-metal single, double or triple bonds. It can be in particular a carbon-metal single bond of σ type: in this case, the hydrocarbon-comprising ligand is an alkyl radical, for example a linear or branched alkyl radical. The term "alkyl radical" is understood to mean a monovalent aliphatic radical originating from the removal of a hydrogen atom in the molecule of an alkane or of an alkane or of an alkyne, for example a methyl ($CH_3$—), ethyl ($C_2H_5$—), propyl ($C_2H_5$—$CH_2$—), neopentyl (($CH_3)_3C$—$CH_2$—), allyl ($CH_2$=CH—$CH_2$—) or acetylene (CH≡C—) radical. The alkyl radical can be, for example, of formula R—$CH_2$—, where R itself represents a linear or branched alkyl radical.

It can also be a carbon-metal double bond of π type: in this case, the hydrocarbon-comprising ligand is an alkylidene radical, for example a linear or branched alkylidene radical. The term "alkylidene radical" is understood to mean a bivalent aliphatic radical originating from the removal of two hydrogen atoms on the same carbon of the molecule of an alkane or of an alkane or of an alkyne, for example a methylidene ($CH_2$=), ethylidene ($CH_3$—CH=), propylidene ($C_2H_5$—CH=), neopentylidene (($CH_3)_3C$—CH=) or alkylidene (($CH_2$=CH—CH=) radical. The alkylidene radical can be, for example, of formula R—CH=, where R represents a linear or branched alkyl radical The carbon-metal bond can also be a triple bond: in this case, the hydrocarbon-comprising ligand is an alkylidyne radical, for example a linear or branched alkylidyne radical The term "alkylidyne radical" is understood to mean a trivalent aliphatic radical originating from the removal of three hydrogen atoms on the same carbon of the molecule of an alkane or of an alkane or of an alkyne, for example an ethylidyne ($CH_3$—C≡), propylidyne ($C_2H_5$—C≡), neopentylidyne (($CH_3)_3C$—C≡) or alkylidyne ($CH_2$=CH—C≡) radical. The alkylidyne radical can be, for example, of formula R—C≡, where R represents a linear or branched alkyl radical. It is preferable to have, among the alkyl, alkylidene and alkylidyne radicals, in particular methyl, ethyl, propyl, isobutyl, neopentyl, allyl, neopentylidene, alkylidene and neopentylidyne radicals.

The metal M of the organometallic precursor (P) can be bonded to two or more identical or different hydrocarbon-comprising ligands chosen from alkyl alkylidene and alkylidyne radicals. In particular, it can be bonded to at least one alkyl radical and to at least one alkylidene or alkylidyne radical.

The preparation of the catalyst comprises a first stage during which the organometallic precursor (P) is dispersed over and grafted to a solid support, as described above. The support, which is preferably a metal oxide or refractory oxide, such as silica, is subjected to a heat treatment which is capable in particular of bringing about a dehydration and/or a dehydroxylation, in particular between 200 and 1100° C., for several hours, for example from 2 to 48 hours, preferably from 10 to 24 hours. The maximum temperature of the heat treatment is preferably below the sintering temperature of the solid support. Thus, for a silica, a dehydration and/or a dehydroxylation can be carried out at a temperature of 200 to 500° C., for example of 300 to 500° C., or else at a temperature ranging from 500° C. to the sintering temperature of the silica, in order in particular to form siloxane bridges at the surface of the support.

The operations of dispersing of the organometallic precursor (P) over the solid support and of grafting the organometallic precursor (P) to the solid support can be carried out by sublimation or by bringing into contact in liquid medium or in solution.

In the case of a sublimation operation, the organometallic precursor (P), used in the solid state, is heated under vacuum and under temperature and pressure conditions which provide for its sublimation and its migration in the vapour state onto the support. The latter is preferably used in pulverulent form or in the form of pellets. The sublimation is carried out in particular between 25 and 300° C., preferably between 50 and 150° C., under vacuum. In particular, the grafting of the organometallic precursor (P) to the support can be monitored using infrared spectroscopic analysis.

In the method which has just been described, the sublimation can be replaced by an operation of bringing into contact and a reaction in liquid or solvent medium. In this case, the organometallic precursor (P) is preferably dissolved in an organic solvent, such as pentane or ether. The reaction is then carried out by suspending the support, preferably in a pulverulent form, in the solution comprising the organometallic precursor (P) or alternatively by any other method which provides contact between the support and the organometallic precursor (P). The reaction can be carried out at room temperature (20° C.) or more generally at a temperature ranging from −80° C. to 150° C. under an inert atmosphere, for example a nitrogen atmosphere.

The excess organometallic precursor (P) which is not attached to the support can be removed, for example by washing or reverse sublimation.

The preparation of the catalyst subsequently comprises a second stage during which the organometallic precursor, dispersed over and grafted to the solid support, is brought into contact with hydrogen or a reducing agent capable of converting the atoms of the metal M to metal hydrides, in particular by hydrogenolysis of the hydrocarbon-comprising ligands bonded to the metal. It is generally a reduction reaction on the metal M attached to the support, which thus has its oxidation state reduced to a value lower than its maximum value. The reaction can take place under an absolute pressure ranging from $10^{-3}$ to 10 MPa and at a temperature ranging from 25 to 400° C., preferably from 100 to 300° C. The reaction can be carried out over a period of time ranging from 1 to 24 h, preferably from 10 to 20 h.

The catalyst can be prepared by other methods using other precursors, in so far as they result in a metal hydride of the metal M which is supported and which is capable of catalysing an alkane metathesis.

Mention may be made, among the preferred catalysts, of tantalum, tungsten or chromium hydrides which are grafted to and dispersed over a silica or a silica/alumina.

Another subject-matter of the present invention is the use of a catalyst capable of catalysing a metathesis of alkanes in a reaction resulting from bringing methane into contact with at least one other starting alkane (A) under conditions which result in the formation of at least one or two final alkanes (B) having a number of carbon atoms less than or equal to that of the starting alkane (A) but at least equal to 2.

The process according to the invention can be carried out batchwise or continuously. It can be carried out in the gas phase, in particular in a mechanically stirred and/or fluidized bed reactor or in a stationary or circulating bed reactor, the bed being composed essentially of the catalyst. The process can also be carried out in the liquid phase, for example in the starting alkane (A) in the liquid state, the catalyst being suspended in the liquid phase.

The process can be carried out in the presence of an inert, liquid or gaseous, agent, such as nitrogen, helium or argon.

The process can be carried out at a temperature ranging from −30 to +400° C., preferably from 0 to 300° C., in particular from 20 to 200° C., under an absolute pressure ranging from $10^{-3}$ to 30 Mpa, preferably from $10^{-1}$ to 20 MPa, in particular from $10^{-1}$ to 10 MPa.

In the process according to the invention, the methane and the starting alkane(s) (A) can be added to the catalyst separately and in any order, or simultaneously by at least two separate introductions, or alternatively premixed and using a single introduction. The methane and the starting alkane(s) (A) can be used in a (methane:starting alkane(s) (A)) molar ratio ranging from 0.1:1 to 500:1, preferably from 1:1 to 200:1, in particular from 1:1 to 100:1.

The proportion of catalyst present in the reaction mixture composed of methane and the starting alkane(s) (A) can be such that the molar ratio of methane to the metal M of the catalyst is from 10:1 to $10^5$:1, preferably from 50:1 to $10^4$:1, in particular from 50:1 to $10^3$:1.

The examples which follow illustrate the present invention.

EXAMPLE 1

Preparation of a Catalyst Based on Supported Tantalum Hydride

A catalyst based on supported tantalum hydride $[Ta]_s$—H is prepared in the following way: tris(neopentyl) neopentylidenetantalum of general formula $Ta[-CH_2-CMe_3]_3[=CH-CMe_3]$ (in which Me represents the methyl radical) is sublimed at 80° C. in a glass reactor over a silica dehydroxylated beforehand at 500° C. and is then grafted by a reaction at 25° C. with the surface hydroxyl groups of the silica, which reaction corresponds to the following equation (6):

$$3\equiv SiOH + 2Ta[-CH_2-CMe_3]_3[=CH-CMe_3] \rightarrow$$
$$\equiv SiO-Ta[-CH_2-CMe_3]_2[=CH-CMe_3] +$$
$$(\equiv SiO)_2-Ta[-CH_2-CMe_3]3CMe_4 \quad (6)$$

The mixture of the neopentylneopentylidenetantalum compounds which are thus obtained, which are dispersed over and grafted to silica:

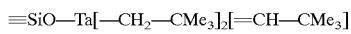

and

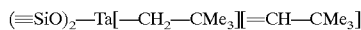

is subsequently treated under hydrogen at atmospheric pressure at 150° C. for 15 h, so as to form supported tantalum hydride species by hydrogenolysis of the neopentyl and neopentylidene ligands.

EXAMPLE 2

Preparation of a Catalyst Based on Supported Tantalum Hydride

A catalyst based on supported tantalum hydride $[Ta]_s$—H is prepared in the following way: a silica is dehydroxylated beforehand at a temperature of 500° C. and then at 1100° C., so as to bring about the appearance at the surface of more or less strained siloxane bridges resulting from the condensation of the hydroxyl groups; tris(neopentyl) neopentylidenetantalum of general formula $Ta[-CH_2-CMe_3]_3[=CH-CMe_3]$ is sublimed at 80° C. and reacts with the residual hydroxyl groups and the siloxane bridges according to the following equation (7):

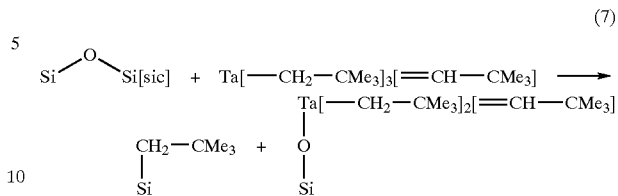

Conversion of the neopentylneopentylidene-tantalum compounds, dispersed over and grafted to silica, to supported tantalum hydrides is carried out as in Example 1 by treatment under hydrogen.

EXAMPLE 3

Preparation of a Catalyst Based on Supported Tungsten Hydride

A catalyst based on supported tungsten hydride $[W]_s$—H is prepared in the following way: tris(neopentyl) neopentylidynetungsten of general formula $W[-CH_2-CMe_3]_3[\equiv C-CMe_3]$ is sublimed at 80° C. in a glass reactor over a silica dehydroxylated beforehand at 500° C. and is then grafted by a reaction at 25° C. with the surface hydroxyl groups of the silica. The mixture of the tungsten compounds which are thus obtained and supported is subsequently treated under hydrogen at atmospheric pressure at 150° C. for 15 h, so as to form supported hydride species by hydrogenolysis of the neopentyl and neopentylidyne ligands.

EXAMPLE 4

Reaction of Methane with Ethane

The tantalum hydride supported on silica $[Ta]_s$—H catalyst (50 mg; content by weight of tantalum=4.89% Ta/$SiO_2$; that is to say, 14 micromol of tantalum) prepared in Example 1 is used.

A reactor with a capacity of 0.28 l comprising the abovementioned catalyst is placed under vacuum, is then filled with a mixture of $^{13}C$-labelled methane and of ethane ($C_2$) (unlabelled) with the following partial pressures (pp):

methane pp ($^{13}C$-labelled)=64.5 kPa
ethane pp=1.2 kPa and is heated at 165° C. under steady state conditions. The reaction products are measured over time under these conditions and are analysed by gas chromatography, optionally coupled with mass spectrometry The results are collated in Table 1.

TABLE 1 results of the reaction between $^{13}C$-labelled methane and ethane ($C_2$)

| Time (h) | % C2 | % C2* | % C2** | Molar ratio of the $^{13}C$ incorporated in ethane to the tantalum |
|---|---|---|---|---|
| 1.5 | 94 | 6 | — | 0.47 |
| 12 | 90 | 10 | — | 0.73 |
| 36 | 87 | 13 | — | 0.88 |

TABLE 1-continued results of the reaction between $^{13}$C-labelled methane and ethane (C$_2$)

| Time (h) | % C2 | % C2* | % C2** | Molar ratio of the $^{13}$C incorporated in ethane to the tantalum |
|---|---|---|---|---|
| 60 | 80 | 20 | — | 1.13 |
| 120 | 67 | 28 | 5 | 1.99 |

% C$_2$: molar percentage of $^{13}$C-unlabelled ethane with respect to the total ethane;
% C2*: molar percentage of singly $^{13}$C-labelled ethane ($^{13}$CH$_3$—CH$_3$) with respect to the total ethane;
% C2**: molar percentage of doubly $^{13}$C-labelled ethane ($^{13}$CH$_3$—$^{13}$CH$_3$) with respect to the total ethane.

The reactions involved in this example as main stage are as follows:

$^{13}$CH$_4$+CH$_3$—CH$_3$→C$_4$+$^{13}$CH$_3$—CH$_3$
$^{13}$CH$_4$+$^{13}$CH$_3$—CH$_3$→CH$_4$+$^{13}$CH$_3$—$^{13}$CH$_3$

It is observed, from Table 1, that the carbon-13 of the methane is gradually incorporated in the ethane molecule, which first becomes singly labelled, then doubly labelled, thereby showing a reaction between the methane and the ethane.

In addition to this main stage, other reactions take place in parallel by conventional metathesis reactions on the labelled or unlabelled ethane according to the equations (1), to form in particular propane, in particular $^{13}$C-labelled propane.

EXAMPLE 5

Reaction of Methane with Ethane

The reaction is carried out exactly as in Example 4, except that use is made of the catalyst prepared in Example 2 (40 mg; content by weight of tantalum=4.89% Ta/SiO$_2$).

A gradual formation of singly $^{13}$C-labelled ethane, then doubly $^{13}$C-labelled ethane, is observed, as in Example 4.

EXAMPLE 6

Reaction of Methane with Ethane

The reaction is carried out exactly as in Example 4, except that use is made of the catalyst prepared in Example 3 (53 mg; content by weight of tungsten=4.96% W/SiO$_2$).

A gradual formation of singly and then doubly $^{13}$C-labelled ethane is observed, as in Example 4.

EXAMPLE 7

Reaction of Methane with Propane

The reaction is carried out exactly as in Example 4, except that ethane is replaced with propane.

It is observed that ethane progressively labelled with $^{13}$C is formed as main stage. In addition to this, other higher alkanes are progressively formed by reactions according to the equation (1).

EXAMPLE 8

Reaction of Methane with n-Butane

The reaction is carried out exactly as in Example 4, except that ethane is replaced with n-butane.

It is observed that ethane and propane, both progressively labelled with $^{13}$C, are simultaneously formed as main stage. Other higher alkanes appear by reactions according to the equation (1).

What is claimed is:

1. A process for the manufacture of alkanes, comprising reacting methane with at least one other starting alkane (A) in the presence of a catalyst based on a metal M capable of catalysing a metathesis of alkanes, which reaction causes cleavage and recombination reactions of the methane and the at least one other starting alkane (A) and results in the formation of at least one or two final alkane(s) (B) having a number of carbon atoms less than or equal to that of the at least one other starting alkane (A) and at least equal to 2.

2. The process of claim 1, wherein the at least one other starting alkane (A) is selected from the group consisting of substituted or unsubstituted acyclic alkanes and substituted cyclic alkanes.

3. The process of claim 1 or 2, wherein the at least one other starting alkane (A) corresponds to the general formula $$C_nH_{2n+2}$$

in which n is an integer ranging from 2 to 60.

4. The process of claim 1 or 2, wherein the at least one other starting alkane (A) is a cycloalkane which is substituted and which corresponds to the general formula $$C_nH_{2n+2}$$

in which n is an integer ranging from 6 to 60.

5. The process of claim 1, wherein the at least one other starting alkane (A) is selected from the group consisting of propane, n-butane, isobutane, n-pentane, isopentane, n-hexane, n-octane, n-nonane and n-decane.

6. The process of claim 1, wherein the at least one other starting alkane (A) is a C$_3$ to C$_{17}$ alkane.

7. The process of claim 1, wherein the at least one other starting alkane (A) is a C$_{18}$ to C$_{60}$ paraffin.

8. The process of claim 1, wherein the catalyst is a hydride of a metal M grafted to and dispersed over a solid support.

9. The process of claim 8, wherein the metal M is selected from the group consisting of transition metals, lanthanides and actinides.

10. The process of claim 9, wherein the metal M is selected from the group consisting of titanium, zirconium, hafnium, vanadium, niobium, tantalum, chromium, molybdenum and tungsten.

11. The process of claim 8, wherein the metal M is at an oxidation state lower than its maximum value.

12. The process of claim 8, wherein the solid support is selected from the group consisting of metal oxides and refractory oxides.

13. The process of claim 12, wherein the metal M is bonded to an oxygen atom of the solid support.

14. The process of claim 8, wherein the catalyst is prepared by:
 (a) dispersing over and grafting to the solid support an organometallic precursor (P) comprising the metal M bonded to at least one hydrocarbon-comprising ligand, then
 (b) treating the solid product resulting from (a) with hydrogen or a reducing agent capable of forming a metal M-hydrogen bond.

15. The process of claim 1, wherein the reaction between methane and the at least one other starting alkane (A) is carried out at a temperature of −30 to +400° under an absolute pressure of 10$^{-3}$ to 30 MPa.

16. The process of claim 1, wherein the reaction between methane and the at least one other starting alkane (A) is carried out in the gas phase in a mechanically stirred and/or fluidized bed reactor or in a stationary or circulating bed reactor, the bed being composed essentially of the catalyst.

17. The process of claim 1, wherein the reaction between methane and the at least one other starting alkane (A) is carried out in the liquid phase, the catalyst being suspended in the liquid phase.

18. The process of claim 1, wherein the methane and the at least one other starting alkane (A) are used in a (methane:starting alkane (A)) molar ratio ranging from 0.1:1 to 500:1.

19. The process of claim 1, wherein the catalyst is present in a reaction mixture of the methane and the at least one other starting alkane (A) in a proportion such that the molar ratio of methane to the metal M of the catalyst is from 10:1 to $10^5$:1.

20. The process of claim 12, wherein the metal M is bonded to at least two oxygen atoms of the solid support.

* * * * *